(12) United States Patent
Salman et al.

(10) Patent No.: US 6,686,497 B1
(45) Date of Patent: Feb. 3, 2004

(54) SYNTHESIS OF 3-ETHOXY-4-ETHOXYCARBONYL PHENYL ACETIC ACID, A KEY ACID SYNTHON OF REPAGLINIDE

(75) Inventors: Mohammad Salman, Haryana (IN); J. Suresh Babu, Haryana (IN); Purna C. Ray, New Delhi (IN); Sujay Biswas, New Delhi (IN); Naresh Kumar, Haryana (IN)

(73) Assignee: Banbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/130,579

(22) PCT Filed: Sep. 11, 2000

(86) PCT No.: PCT/IB00/01288

§ 371 (c)(1),
(2), (4) Date: Sep. 20, 2002

(87) PCT Pub. No.: WO01/35900

PCT Pub. Date: May 25, 2001

(30) Foreign Application Priority Data

Nov. 16, 1999 (IN) ........................................ 1483/DEL/99

(51) Int. Cl.$^7$ ................................................ C07C 69/76
(52) U.S. Cl. ........................ 560/64; 546/234; 514/212; 514/326; 514/331; 514/619
(58) Field of Search ............................ 560/64; 546/234; 514/212, 326, 619, 331

(56) References Cited

U.S. PATENT DOCUMENTS

| 5,216,167 A | 6/1993 | Grell et al. | 546/234 |
| 5,312,924 A | 5/1994 | Grell et al. | 546/234 |

FOREIGN PATENT DOCUMENTS

| WO | WO 93/00337 | 1/1993 | 295/12 |

OTHER PUBLICATIONS

Grell et al, J. Med. Chem., 1988, vol. 41, pp. 5219–5246.*
Grell et al., *Repaglinide and Related Hypoglycemic Benzoic Acid Derivatives*, J. Med. Chem., 1998, 41, pp. 5219–5246.

* cited by examiner

*Primary Examiner*—Alan L. Rotman
*Assistant Examiner*—Hector M Reyes
(74) *Attorney, Agent, or Firm*—Jayadeep R. Deshmukh, Esq.; William D. Hare, Esq.; George E. Heibel, Esq.

(57) ABSTRACT

The present invention relates to a new and industrially advantageous process for the preparation of 3-ethoxy-4-ethoxy-carbonyl-phenyl acetic acid. This compound is a key intermediate for the synthesis of Repaglinide, an oral hypoglycemic agent.

18 Claims, No Drawings

SYNTHESIS OF 3-ETHOXY-4-ETHOXYCARBONYL PHENYL ACETIC ACID, A KEY ACID SYNTHON OF REPAGLINIDE

FIELD OF THE INVENTION

The present invention relates to a new and industrially advantageous process for the preparation of 3-ethoxy-4-ethoxycarbonyl-phenyl acetic acid of Formula I:

FORMULA-I

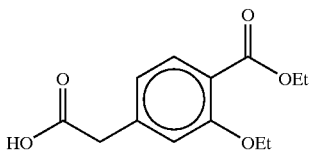

This compound is a key intermediate for the synthesis of Repaglinide of Formula II:

FORMULA-II

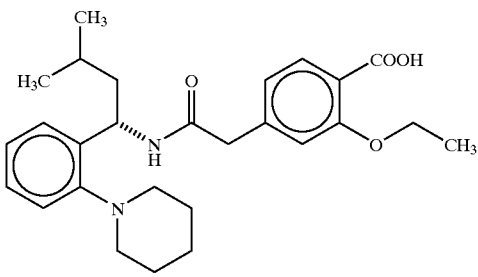

an oral hypoglycemic agent.

BACKGROUND OF THE INVENTION

Chemically, Repaglinide is S (+) 2-ethoxy-4-[N-{1-(2-piperidinophenyl)-3-methyl-1-butyl}-aminocarbonylmethyl]benzoic acid (Formula II) and is known from U.S. Pat. Nos. 5,216,167 and 5,312,924. Repaglinide is first member of a new class of oral hypoglycemic agents (Meglitinides) for type II non-insulin dependent diabetes mellitus (NIDDM). It stimulates the secretion of insulin from beta cells in the pancreas, acting via calcium channels. Hypoglycemic events are less with repaglinide as compared with other anti-diabetic agents. It offers significantly better biological profile as compared with sulphonyl urea class of hypoglycemic agents, and has been approved by the U.S. FDA for treatment of non-insulin dependent diabetes mellitus (type-II diabetes).

A previously known method for the synthesis of intermediate, 3-ethoxy-4-(ethoxycarbonyl)-phenylacetic acid, of Formula I, was reported in J.Med. Chem; 41, 5219 (1998) which involves five steps with an alleged overall yield of about 21% of theory. These steps include: (1) alkylation of 4-methylsalicylic acid of Formula III

FORMULA-III

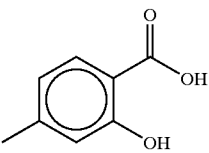

with ethyl bromide in acetone, in the presence of potassium carbonate, at 150° C. for 30 hours in an autoclave to give ethyl 2-ethoxy-4-methyl-benzoate of Formula IV

FORMULA-IV

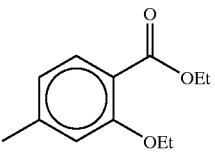

(2) bromination with N-bromosuccinimide (NBS) in carbon tetrachloride in the presence of azo-bis-isobutyronitrile (AIBN) to give ethyl 4-bromomethyl-2-ethoxy-benzoate of Formula V

FORMULA-V

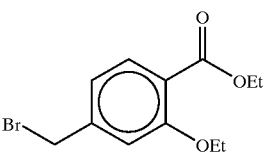

(3) cyanation of bromo intermediate of Formula V with sodium cyanide in dichloromethane for 43 hours to give ethyl 4-cyanomethyl-2-ethoxybenzoate of Formula VI

FORMULA-VI

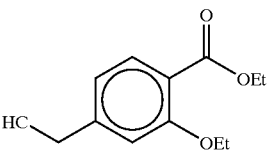

(4) selective hydrolysis of cyanomethyl intermediate (of Formula VI) with gaseous hydrochloric acid in ethanol under reflux to give ethyl 2-ethoxy-4-(ethoxycarbonylmethyl)benzoate of Formula VII

FORMULA-VII

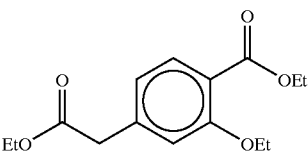

and (5) hydrolysis of di-ester of Formula VII with aqueous sodium hydroxide to yield the desired intermediate, 3-ethoxy-4-(ethoxycarbonyl)phenyl acetic acid of Formula I.

The above mentioned method described in the prior art for the manufacture of the desired compound of Formula I suffers from the following limitations:
- The process is lengthy involving five steps with an overall yield of about 21% of theory.
- The reaction conditions are unsafe and inconvenient to handle at a commercial scale, as it involves high temperature (150° C. for O-alkylation) and longer reaction times.
- The process requires raw materials which are toxic and difficult to handle at commercial scale, e.g. sodium cyanide, carbon tetrachloride and gaseous hydrochloric acid.

3

The process requires specialized equipment such as an autoclave (to carry out O-alkylation at 150° C. at step-I).

SUMMARY OF THE INVENTION

It is an object of the present invention to provide a simple, commercially viable, and efficient process for the preparation of 3-ethoxy-4-ethoxycarbonyl-phenyl acetic acid of Formula I in 59–72% over all yield. It is a further object of the present invention to avoid the use of hazardous, toxic and commercially difficult-to-handle raw materials.

More particularly, the present invention relates to a process for the preparation of 3-ethoxy-4-(ethoxycarbonyl) phenyl acetic acid of Formula I, comprising reacting 4-methylsalicylic acid of Formula III, with ethylbromide in a dipolar aprotic solvent at a selected temperature within a range of ambient to 100° C., preferably 30–40° C. during a period of one to several hours. The suitable dipolar aprotic solvent is selected from the group consisting of dimethylsulphoxide, N, N-dimethyl formamide, sulfolane and N-methyl-1-pyrrolidone. The reaction is carried out in the presence of an inorganic base, preferably selected from the group consisting of potassium carbonate and sodium carbonate. The reaction is worked up following the conventional method to afford ethyl 2-ethoxy-4-methylbenzoate of Formula IV in practically quantitative yield. The compound of Formula IV is then reacted with lithium diisopropyl amide (LDA) of Formula VIII,

  FORMULA—VIII which in turn is prepared by reacting n-butyllithium and diisopropylamine in anhydrous tetrahydrofuran as a solvent by following the methods known in the prior art. More particularly, ethyl 2-ethoxy-4-methyl-2-benzoate of Formula IV is reacted with lithium diisopropylamide (LDA) of Formula VII at –40 to –80° C., preferably at –60 to –80° C. for 0.5 to several hours and subsequent decomposition of carbanion with carbondioxide. Preferably, the reaction of compounds of Formula IV and VII is carried out in the presence of a suitable diploar aprotic co-solvent which is selected from the group consisting of hexamethylphosphoramide (HMPA), 1,3-dimethyl-3,4,5,6-tetrahydro-2-(1H) pyrimidinone (DMPU); 1,3-dimethyl-2-imidazolidinone (DMEU) and tetramethyl urea. The reaction mixture is then decomposed in water. The aqueous layer is then acidified with mineral acid comprising sulphuric acid, hydrochloric acid etc to an acidic pH, preferably at pH about 2. The desired compound, 3-ethoxy-4-(ethoxycarbonyl)phenyl acetic acid of Formula I is isolated at this pH by conventional methods including extraction with a suitable solvent which is selected from the group consisting of dichloromethane, dichloroethane, chloroform, ether, isopropyl ether and toluene.

In the following section several preferred embodiments are described by way of examples to illustrate the process of this invention. However, these are not intended in any way to limit the scope of the present invention.

DETAILED DESCRIPTION OF THE INVENTION

EXAMPLE 1

Preparation of 3-Ethoxy-4-(ethoxycarbonyl)phenyl Acetic Acid

STEP 1: Preparation of Ethyl-2-ethoxy-4-methylbenzoate

Potassium carbonate (68.0 g, 0.492 mole) was added to a well-stirred solution of 4-methylsalicylic acid (25 g, 0.164 mole) in dimethylsulfoxide (75 ml). The mixture was stirred at 35–40° C. and 1st lot of ethyl bromide (27.0 g, 0.247 mole) was added slowly over a period of 30 minutes then stirred for two hours and a second lot of ethyl bromide (27.0 g, 0.247 mole) was added over a period of 30 minutes at 35–40° C. The reaction mixture was further stirred at 35–40° C. for eight hours, cooled to 20–25° C., and diluted with dichloromethane (50 ml). The inorganics were removed by filtration and washed with dichloromethane. The combined filtrate and washings were diluted with water (50 ml), stirred for 30 minutes, and the organic layer was separated. The aqueous layer was further extracted with dichloromethane and the combined dichloromethane layer was washed with water (2×50 ml). The solvent was removed under vacuum to afford ethyl 2-ethoxy-4-methylbenzoate 34.2 g (quantitative yield).

STEP—2: Preparation of 3-Ethoxy-4-(ethoxycarbonyl) phenyl Acetic Acid

Under an atmosphere of nitrogen, n-butyllithium (25 ml, 15% w/w solution in hexane) was added to a solution of diisopropylamine (3.6 g) in tetrahydrofuran (30 ml) at –30° C. The mixture was stirred at –30° C. for 30 minutes, cooled to –75° C., and hexamethylphosphoramide (HMPA, 10 g) was added slowly. A solution of ethyl 2-ethoxy-4-methylbenzoate (5 g) in tetrahydrofuran (10 ml) was then added at –75° C. and the mixture was stirred for two hours. Carbon dioxide gas was then purged into the reaction mixture at –75° C. till complete decolorization. The reaction mixture was then stirred at –75 to –70° C. for 30 minutes and then brought to 10° C., diluted with water (50 ml), and extracted with ether. The aqueous layer was acidified with 10% aqueous sulphuric acid to pH ~2 and extracted with dichloromethane. The combined dichloromethane layer was washed with water and concentrated in vacuo. The oily product so obtained was re-dissolved in ether (50 ml) and washed with water. The ethereal layer was then concentrated in vacuo to afford a thick oil which solidified on keeping at room temperature to afford 3-ethoxy-4-(ethoxycarbonyl) phenyl acetic acid 4.4 g (72.7%).

EXAMPLE 2

STEP—3: Preparation of 3-Ethoxy-4-(ethoxycarbonyl) phenyl Acetic Acid

Under an atmosphere of nitrogen, n-butyllithium (50 ml, 15% w/w solution in hexane) was added to a solution of diisopropylamine (7.25 g) in tetrahydrofuran (90 ml) at –30° C. The mixture was stirred at –30° C. for 30 minutes, cooled to –75° C., and 1,3-dimethyl-3,4,5,6-tetrahydro-2(1H)-pyrimidinone (DMPU, 30 ml), was added slowly. A solution of ethyl 2-ethoxy-4-methylbenzoate (10 g) in tetrahydrofuran (10 ml) was then added at –75° C. and the mixture was stirred for two hours. Carbon dioxide gas was then purged into the reaction mixture at –75° C. till complete decolorization. The reaction mixture was then brought to room temperature, diluted with water (100 ml), and extracted with dichloromethane (100 ml). The aqueous layer was acidified with 10% aqueous sulphuric acid to pH 1.95 and extracted with toluene. The combined toluene layer was washed with water and concentrated in vacuo. Crystallisation with ethyl acetate/petroleum ether afforded (3-ethoxy-4-ethoxycarbonyl)-phenyl acetic acid 7.2 g (59.5%).

While the present invention has been described in terms of its specific embodiments, certain modifications and equivalents will be apparent to those skilled in the art and are intended to be included within the scope of this invention, which is to be limited only by the scope of the appended claims.

We claim:

1. A process for the preparation of 3-ethoxy-4-(ethoxycarbonyl)phenylacetic acid, the process comprising:
    reacting ethyl 2-ethoxy-4-methylbenzoate with lithium diisopropylamide; and quenching the resulting carbanion with carbon dioxide to obtain the 3-ethoxy-4-(ethoxycarbonyl)phenylacetic acid.

2. The process of claim 1, wherein in the reaction is performed in the presence of tetrahydrofuran as a solvent.

3. The process of claim 1, wherein in the reaction is performed in the presence of a dipolar aprotic co-solvent.

4. The process of claim 2, wherein in the reaction is performed in the presence of a dipolar aprotic co-solvent.

5. The process of claim 3, wherein in the dipolar aprotic co-solvent is selected from the group comprising one or more of hexamethylphosphoramide, 1,3-dimetliyl 3,4,5,6-tetrahydro-2(1H) pyrimidinone, 1,3-dimethyl imidazolidinone, tetramethyl urea, and mixtures thereof.

6. The process of claim 4, wherein in the dipolar aprotic co-solvent is selected from the group comprising one or more of hexamethylphosphorarmide, 1,3-dimethyl 3,4,5,6-tetrahydro-2(1H) pyrimidinone, 1,3-dimethyl imidazolidinone, tetramethyl urea, and mixtures thereof.

7. The process of claim 1, wherein the reaction of ethyl 2-ethoxy-4-methylbenzoate with lithium diisopropyl amide is performed at a temperature of about −30 to −100° C.

8. The process of claim 7, wherein the temperature is about −60 to −80° C.

9. The process of claim 1, wherein the 3-ethoxy-4-(ethoxycarbonyl)phenylacetic acid is recovered from an aqueous medium at an acidic pH by extracting the reaction mixture with a solvent.

10. The process of claim 9, wherein the pH is about 2.

11. The process of claim 9, wherein the extraction solvent comprises one or more of dichloromethane, dichloroethane, chloroform, ether, isopropyl ether, toluene, and mixtures thereof.

12. The process of claim 1, wherein the ethyl 2-ethoxy-4-methylbenzoate is prepared by reacting 4-methylsalicylic acid with ethylbromide in a dipolar aprotic solvent in the presence of an inorganic base to obtain the ethyl 2-ethoxy-4-methylbenzoate.

13. The process of claim 12, wherein the dipolar aprotic solvent comprises one or more of dimethyl sulphoxide, N,N-(dimethylformamide, sulfolane, N-methyl pyrrolidone, and mixtures thereof.

14. The process of claim 12, wherein the inorganic base comprises one or both of sodium carbonate and potassium carbonate.

15. The process of claim 12, wherein the reaction is performed at a temperature of about 25° C. to about 100° C.

16. The process of claim 15, wherein the temperature is about 25° C. to about 40° C.

17. A method of synthesizing a benzoic acid-based group of hypoglycemic agents, the method comprising using the 3-ethoxy-4-(ethoxycarbonyl)phenylacetic acid prepared by the process of claim 1 in the synthesis.

18. The process of claim 17, wherein the benzoic acid-based hypoglycemic agent comprises Repaglinide.

* * * * *

UNITED STATES PATENT AND TRADEMARK OFFICE
CERTIFICATE OF CORRECTION

PATENT NO.    : 6,686,497 B1
DATED         : February 3, 2004
INVENTOR(S)   : Salman et al.

It is certified that error appears in the above-identified patent and that said Letters Patent is hereby corrected as shown below:

Title page,
Item [73], Assignee, "Banbaxy Laboratories Limited" should read -- Ranbaxy Laboratories Limited --
Item [57], ABSTRACT,
Line 3, "ethoxy-carbonyl-phenyl" should read -- ethoxycarbonyl-phenyl --

Column 2,
Lines 35 through 40, Formula VI,

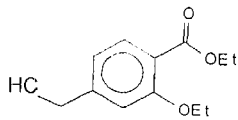 should read 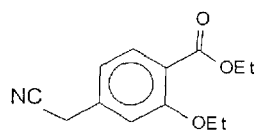

FORMULA - VI                    FORMULA - VI

Column 3,
Line 39, "Formula VI and VII" should read -- Formula VI and VIII --

Column 6,
Line 12, "N,N-(dimethylformamide" should read -- N,N-dimethylformamide --

Signed and Sealed this

Thirty-first Day of August, 2004

JON W. DUDAS
*Director of the United States Patent and Trademark Office*